United States Patent
Knoll et al.

(10) Patent No.: US 8,920,329 B2
(45) Date of Patent: Dec. 30, 2014

(54) DISPOSABLE SENSOR DEVICE AND MONITORING SYSTEM WITH TRIMMING ELEMENT

(75) Inventors: Reinhold Knoll, Munich (DE); Frederic Michard, Gex (FR); Matthias Fahle, Munich (DE); Tobias Thomamüller, Bruckmuhl (DE); Ulrich Pfeiffer, Munich (DE)

(73) Assignee: Edwards Lifesciences IPRM AG, Nyon (CH)

( * ) Notice: Subject to any disclaimer, the term of this patent is extended or adjusted under 35 U.S.C. 154(b) by 1290 days.

(21) Appl. No.: 12/529,010

(22) PCT Filed: Feb. 19, 2008

(86) PCT No.: PCT/EP2008/001289
§ 371 (c)(1),
(2), (4) Date: Apr. 12, 2010

(87) PCT Pub. No.: WO2008/104307
PCT Pub. Date: Sep. 4, 2008

(65) Prior Publication Data
US 2010/0198085 A1    Aug. 5, 2010

(30) Foreign Application Priority Data
Feb. 27, 2007   (DE) .................. 10 2007 009 573

(51) Int. Cl.
*A61B 5/02* (2006.01)
*A61B 5/0215* (2006.01)
*A61B 5/00* (2006.01)

(52) U.S. Cl.
CPC ....... *A61B 5/0215* (2013.01); *A61B 2560/0214* (2013.01); *A61B 2560/045* (2013.01); *A61B 2562/227* (2013.01); *A61B 5/002* (2013.01)
USPC ....................................................... 600/485

(58) Field of Classification Search
USPC ......... 600/481, 483–486, 500–509, 513, 526, 600/547, 561, 488–497; 324/538, 539, 324/115–116, 460, 601, 602, 609, 610
See application file for complete search history.

(56) References Cited

U.S. PATENT DOCUMENTS 4,712,179 A * 12/1987 Heimer ........................... 607/27
4,945,762 A *  8/1990 Adamic, Jr. .............. 73/862.622
(Continued)

FOREIGN PATENT DOCUMENTS

EP    1169965 A1    1/2002
GB    2349283       10/2000
(Continued)

OTHER PUBLICATIONS

International Search Report, PCT/EP2008/001289, Aug. 6, 2008.
(Continued)

*Primary Examiner* — Jacqueline Cheng
*Assistant Examiner* — Puya Agahi
(74) *Attorney, Agent, or Firm* — Michael Crapenhoft

(57) ABSTRACT

The invention relates to a disposable sensor device (51) for patient monitoring comprising a sensor (52) for providing an electric quantity based on a quantity to be detected, a first signal terminal (54) for providing a tap for the electric quantity, a first supply terminal (53) for supplying the sensor with an electrical supply quantity, a first connector for accommodating the first signal terminal (54) and the first supply terminal (53), a second signal terminal (56) for providing a further tap for the electric quantity, and a second connector for accommodating at least the second signal terminal (56). The invention further relates to a disposable sensor device for patient monitoring comprising a sensor (7) for providing an electric quantity based on a quantity to be detected; a first signal terminal (22) for providing a tap for the electric quantity; a first connector (A) for accommodating the first signal terminal, wherein the first connector (A) is provided with a trimming element (R2) which simulates the influence of a selectively attachable first monitoring device (1) on a measuring of the electric quantity, wherein the trimming element (R2) is electrically effective depending on a connector structure of a corresponding further connector (B, C) to be coupled with the first connector (A).

18 Claims, 5 Drawing Sheets

(56) References Cited

U.S. PATENT DOCUMENTS

| | | |
|---|---|---|
| 5,193,547 A | 3/1993 | Evans, II et al. |
| 5,568,815 A * | 10/1996 | Raynes et al. ............ 600/485 |
| 5,929,624 A * | 7/1999 | Ricq et al. ................ 324/67 |
| 6,563,866 B1 | 5/2003 | Gutzmer |
| 6,697,656 B1 * | 2/2004 | Al-Ali ...................... 600/323 |
| 7,550,981 B2 * | 6/2009 | Merry ....................... 324/714 |
| 2002/0149984 A1 * | 10/2002 | Nishikawa et al. ........ 365/207 |
| 2003/0105404 A1 | 6/2003 | Galen et al. |
| 2004/0027872 A1 * | 2/2004 | Nishikawa et al. ........ 365/200 |
| 2004/0142602 A1 * | 7/2004 | Kamei et al. ............... 439/700 |
| 2004/0147847 A1 | 7/2004 | Ng et al. |
| 2004/0199409 A1 | 10/2004 | Brown |
| 2004/0220650 A1 * | 11/2004 | Houben et al. ............ 607/116 |
| 2005/0065417 A1 | 3/2005 | Ali et al. |
| 2006/0009699 A1 | 1/2006 | Roteliuk |
| 2007/0197922 A1 * | 8/2007 | Bradley et al. ............ 600/488 |
| 2008/0129143 A1 * | 6/2008 | Cook et al. ................ 310/312 |
| 2010/0125114 A1 * | 5/2010 | Williams et al. .......... 524/231 |

FOREIGN PATENT DOCUMENTS

| | | |
|---|---|---|
| WO | 9847424 | 10/1998 |
| WO | 0118835 A1 | 3/2001 |
| WO | 0154298 | 7/2001 |

OTHER PUBLICATIONS

European Search Report, Jan. 20, 2010.
European Office Action, Sep. 25, 2012.
European Search Report, Oct. 11, 2010.
European Office Action, Jan. 31, 2013.

* cited by examiner

DISPOSABLE SENSOR DEVICE AND MONITORING SYSTEM WITH TRIMMING ELEMENT

This application is a 371 of International Application No. PCT/EP2008/001289, filed Feb. 19, 2008, which claims priority to German Application No. 102007009573.4 filed Feb. 27, 2007, the contents of which are incorporated herein by reference.

BACKGROUND OF THE INVENTION

The present invention relates to disposable sensor devices for patient monitoring such as an arterial blood pressure sensor device, a pulse contour cardiac output device and the like. The present invention is further related to monitoring systems for such disposable sensor devices.

In patient monitoring there are situations wherein multiple monitoring devices are needed which are dealing with the same parameter. For example, there may be some need to receive the respective signal by a bedside monitor and by a portable device in parallel wherein both should be able to read the parameter of interest. So far, each monitoring device, e.g. the bedside monitoring device and the portable measurement device, uses a separate sensor device. The multiple sensor devices may be closely spaced to detect the same or at least similar results, as e.g. described in US 2006/0009699.

Mostly, the sensor device needs some kind of excitation voltage, i.e. a supply DC or AC voltage. Then, the sensor device delivers a detector signal which depends on the excitation voltage and the parameter which is to be analyzed in the monitoring system.

To provide two sensor devices of the same kind for being read out by two different monitoring devices leads to a bulky shape on the sensor's side. Furthermore, the increased space volume may cause a worse frequency response in case an AC excitation voltage is used. Even if the two sensor devices are closely spaced they are not located at the same heart level such that in case of pressure sensor devices different arterial pressure values would be obtained.

It is therefore an object of the present invention to provide a disposable sensor device and a monitoring system which allows to monitor a measured parameter of patient by two or more monitoring devices thereby avoiding the drawbacks of the prior art.

This object has been achieved by the disposable sensor devices according to claims 1 and 7 and the monitoring systems according to further independent claims.

Further embodiments of the present invention are indicated in the depending subclaims.

BRIEF SUMMARY OF THE INVENTION

According to one aspect a disposable sensor device for patient monitoring is provided. The disposable sensor device comprises a sensor for providing an electric quantity based on a quantity to be detected, a first signal terminal for providing a tap for the electric quantity, a first supply terminal for supplying the sensor with an electrical supply quantity, and a first connector for accommodating the first signal terminal and the first supply terminal. A second signal terminal for providing a further tap for the electric quantity and a second connector for accommodating at least the second signal terminal are provided.

Furthermore, the sensor may be provided as a bridge circuit or any other analogue electric measurement circuit. The bridge circuit could be a Wheatstone full or half bridge e.g. with resistors.

Moreover, the second connector further may include a second supply terminal for tapping the supply quantity provided via the first connector.

According to another aspect, a monitoring system for patient monitoring is provided. The monitoring system comprises the above disposable sensor device, a first monitoring device connectable to the first connector for tapping the electric quantity via the first signal terminal and for supplying the electrical supply quantity via the first supply terminal.

A second monitoring device may be connectable to the second connector for tapping the electric quantity via the second signal terminal.

Furthermore, it may be provided a monitoring system comprising the above disposable sensor device, a first monitoring device connectable to the first connector for tapping the electric quantity via the first signal terminal and for supplying the electrical supply quantity via the first supply terminal, and a second monitoring device connectable to the second connector for tapping the electric quantity via the second signal terminal, wherein the second monitoring device is further adapted to tap the electrical supply quantity supplied by the first monitoring device via the second supply terminal, wherein the second monitoring device includes an excitation sensing circuit adapted to sense whether or not an electrical supply quantity is applied on the second supply terminal and to further supply an electrical supply quantity via the second supply terminal to the disposable sensor device in case no electrical supply quantity can be sensed.

According to a further aspect a disposable sensor device for patient monitoring is provided. The sensor device comprises a sensor for providing an electric quantity based on a quantity to be detected, a first signal terminal for providing a tap for the electric quantity, and a first connector for accommodating the first signal terminal. The first connector is provided with a trimming element which simulates the influence of a selectively attachable first monitoring device on a measuring of the electric quantity, wherein the trimming element is electrically effective depending on a connector structure of a corresponding further connector to be coupled with the first connector.

Moreover, the electric quantity may be applied between the first and a second signal terminals of the first connector, wherein the trimming element is applied between the first and a third signal terminals of the first connector, wherein depending on the connector structure of the corresponding further connector, either the first and second signal terminals are tapped and the third signal terminal remains untapped or the first and a shortcut second and third signal terminals of the first connector are tapped.

Moreover, the sensor may comprise a Wheatstone-Bridge circuit or any other analogue electric measurement circuit.

According to an embodiment the sensor has a pressure sensor for measuring an arterial pressure of a patient.

A first excitation terminal may be provided in the first connector to apply an excitation voltage to the sensor. The excitation voltage may be applied between the first and a second excitation terminals of the first connector, wherein a further trimming element is applied between the first and a third excitation terminal of the first connector, wherein depending on the connector structure of the corresponding further connector, either the first and second excitation terminals are connected with an excitation voltage and the third excitation terminal remains unconnected or the first and a shortcut second and third excitation terminals are connected with the excitation voltage.

According to a further aspect a monitoring system for patient monitoring is provided. The monitoring system comprises a disposable sensor device as mentioned above and a first monitoring device for tapping the electric quantity, having a second connector to match with the first connector, wherein the second connector has a connector structure depending on which the trimming element of the first connector is electrically effective.

Furthermore, the electric quantity may be applied between the first and a second signal terminal of the first connector, wherein the trimming element is applied between the first and a third signal terminals of the first connector, wherein the second connector has a terminal contact to shortcut the second and third signal terminals of the first connector in a plugged condition such that the trimming element is electrically effective.

Moreover, an excitation voltage may be applied between first and second excitation terminals of the first connector, wherein a further trimming element is applied between the first and a third excitation terminal of the first connector, wherein the second connector has an excitation terminal contact which is adapted to provide the excitation voltage from the first monitoring device and to shortcut the second and third excitation terminal to both connect them with the excitation voltage in a plugged condition.

According to a further aspect a monitoring system for patient monitoring is provided. The monitoring system comprises a disposable sensor device as mentioned above, and a second monitoring device for tapping the electric quantity, having a third intermediate connector to match with the first connector, wherein the third connector has a connector structure such that, when the first and second connectors are in a plugged condition, the trimming element of the first connector is electrically ineffective.

The electric quantity may be applied between the first and a second signal terminal of the first connector, wherein the trimming element is applied between the first and a third signal terminal of the first connector, wherein the third connector has a terminal contact to only contact the second signal terminal but not the third signal terminal of the first connector in the plugged condition such that the trimming element is electrically ineffective.

An excitation voltage may be further applicable between first and second excitation terminals of the first connector, wherein a further trimming element is applied between the first and a third excitation terminal of the first connector, wherein the third connector has an excitation terminal contact which is adapted to provide the excitation voltage from the second monitoring device and to only contact the second excitation terminal but not the third excitation terminal of the first connector in the plugged condition such that the further trimming element is electrically ineffective.

According to a further aspect a monitoring system for patient monitoring is provided. The monitoring system comprises a disposable sensor device as mentioned above, a first monitoring device for tapping the electric quantity, having a second connector to match with the first connector, wherein the second connector has a connector structure such that, when the first and second connectors are in a plugged condition, the trimming element of the first connector is electrically effective, and a second monitoring device for tapping the electric quantity, having a third intermediate connector having two outlets to respectively match with the first and the second connector, wherein the second connector has a connector structure such that, when the first and second connectors are in a plugged condition, the trimming element of the first connector is electrically ineffective, wherein the third connector has a connector structure such that when the second and third connectors are in a plugged condition, the second monitoring device receives the electrical quantity passed through the third connector.

Furthermore, the electric quantity may be applied between the first and a second signal terminal of the first connector, wherein the trimming element is applied between the first and a third signal terminal of the first connector, wherein the second connector has a terminal contact which is adapted to shortcut the second and third signal terminals of the first connector in the plugged condition of the first and second connectors such that the trimming element is electrically effective, wherein the third connector has a terminal contact which is adapted to only contact the second signal terminal but not the third signal terminal of the first connector in the plugged condition of the first and third connector such that the trimming element is electrically ineffective.

An excitation voltage may be applicable between first and second excitation terminals of the first connector, wherein a further trimming element is applied between the first and a third excitation terminal of the first connector, wherein the second connector has an excitation terminal contact which is adapted to shortcut the second and third excitation terminals to both connect them with the excitation voltage in a plugged condition, wherein the third connector has an excitation terminal contact which is adapted to only contact the second excitation terminal but not the third excitation terminal of the first connector in the plugged condition of the first and the third connector such that the further trimming element is electrically ineffective, wherein the third connector further has a connector structure such that when the first, second and third connectors are in a plugged condition, the second monitoring device is adapted to supply the excitation voltage to the sensor via the third connector.

An excitation supply unit may be provided in the second monitoring unit which is adapted to detect, when the first and third connector are in the connected condition, an appliance of an excitation voltage on the first and second excitation terminals of the first connector, and in case that no excitation voltage is applied on the first and second excitation terminals of the first connector the excitation supply unit supplies an excitation voltage via the third connector to the first connector otherwise the excitation supply unit does not supply any excitation voltage.

Moreover, the second monitoring device may be adapted to monitor the quantity to be detected for the case the trimming element is electrically effective.

BRIEF DESCRIPTION OF THE DRAWINGS

Preferred embodiments of the present invention are described in detail in conjunction with the accompanying drawings, in which same reference signs indicated elements having the same or similar functionality and in which.

DETAILED DESCRIPTION

Figure 1:
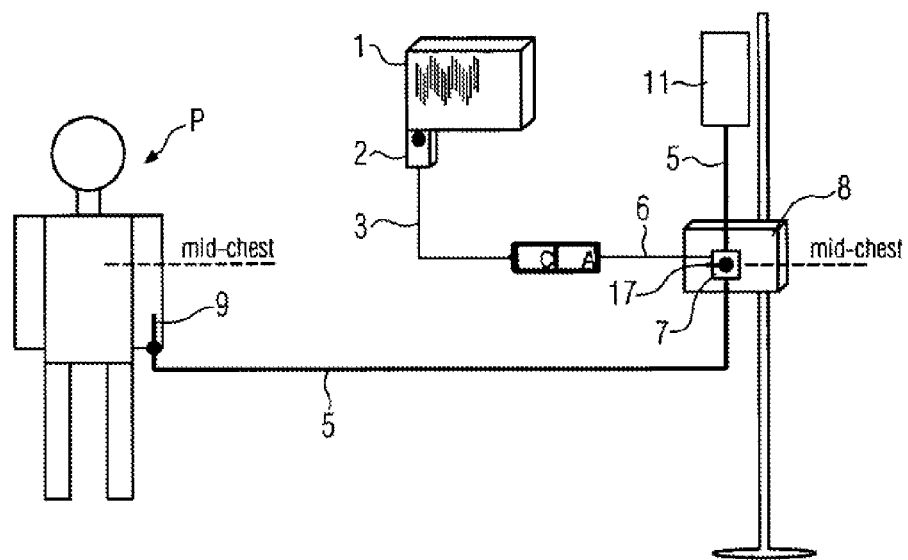
FIG. 1 shows schematically a configuration of a monitoring system according to an embodiment of the present invention.

In FIG. 1 a possible configuration of a monitoring system in a first configuration is disclosed. The monitoring system includes as a first monitoring device a bedside monitor (BSM) 1 for receiving, storing and/or visualizing patient-related data of a patient P. In the illustrated example, the bedside monitor 1 is directly coupled with an arterial pressure module 2 which receives a sensor signal from a disposable pressure transducer (DPT) 7 as a sensor via a cable connection. The arterial pressure module 2 receives the sensor signals and provides a communication of pressure information obtained with the sensor signal to the bedside monitor 1.

An arterial catheter 9 is placed inside the patient P and is coupled with a reservoir 11 via a respective tubing 5. The tubing 5 is configured to supply an infusion liquid from the reservoir 11 to the patient's body. The tubing 5 is lead through an organizer plate 8 which is preferably located at mid-chest level of the patient. A stop cock 17 for disconnecting the reservoir 11 from the catheter 9 is placed on the organizer plate 8. In proximity to the stop cock 17 at the mid-chest level a pressure transducer 7 as a sensor device is placed at the tubing 5 to detect the pressure of the infusion liquid within the tubing 5. The infusion liquid in the tubing 5 transmits the blood pressure in the patient's arterial vessels to the pressure transducer 7 at the organizer plate 8.

The cable connection between the bedside monitor 1 and the pressure transducer 7 includes a connection cable 3 which is connected or connectable to the bedside monitor 1 and which is provided with a third connector C, further referenced as BSM plug C. The pressure transducer 7 is provided with a pressure transducer cable 6 and provided with a first connector A further referred to as transducer plug A. Transducer plug A and BSM plug C can be coupled to provide electrical connections between the bedside monitor 1 and the pressure transducer 7.

Figure 2:
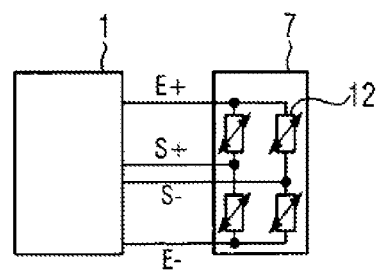
FIG. 2 shows schematically the electrical interconnections between the bedside monitor and the disposable pressure transducer.

In FIG. 2 it is schematically shown the electrical interconnections between the bedside monitor 1 and the disposable pressure transducer 7 as well as a structure of an exemplary pressure transducer. In the given example, the disposable pressure transducer 7 has a number of four pressure detecting elements 12 which are coupled to form a Wheatstone bridge as it is well-known in the art, to increase detection sensitivity. The Wheatstone bridge receives an excitation voltage via excitation lines E+, E− which may be a DC voltage in case of resistive detecting elements 12 and which may be an AC voltage having a predefined oscillation frequency and magnitude in case the detecting elements 12 are capacitive or inductive detecting elements. From the output nodes of the Wheatstone bridge sensor signals S+, S− are tapped via signal lines by the bedside monitor 1. The sensor signals S+, S− depend on the pressure to be detected according to the states of the detecting elements 12 as well as on the excitation voltage. Instead of pressure transducer any kind of sensors which provide a detectable sensor signal can be applied with each embodiment of the present invention.

Figure 3:
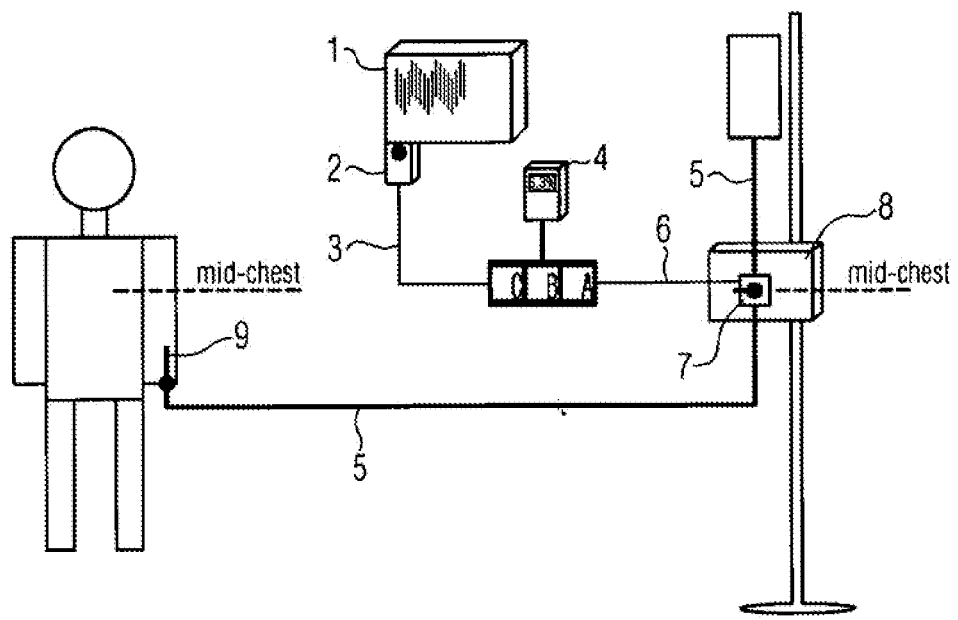
FIG. 3 shows schematically a further configuration of a monitoring system according to the embodiment of FIG. 1.

In cases of a situation wherein in patient monitoring multiple measurement devices are needed to e.g. detect the blood pressure of the patient P the monitoring system proposes a way to further use the pressure transducer 7 as the sensor device for a portable measurement device 4 which is to be further connected with the pressure transducer 7. FIG. 3 shows schematically a second configuration of the monitoring system wherein the portable measuring device 4 is connected with the pressure transducer 7.

The portable measurement device 4 is provided via a measurement cable with an intermediate connector B further referred to as intermediate plug B. The measurement cable includes as described above excitation lines and signal lines to supply the pressure transducer 7 and to receive the sensor signal from the pressure transducer 7, respectively. The intermediate plug B is adapted to couple the portable measurement device 4 with the cable connection between the bedside monitor 1 and the pressure transducer 7. The intermediate plug B is coupled in between the BSM plug C and the transducer plug A.

Figure 4:
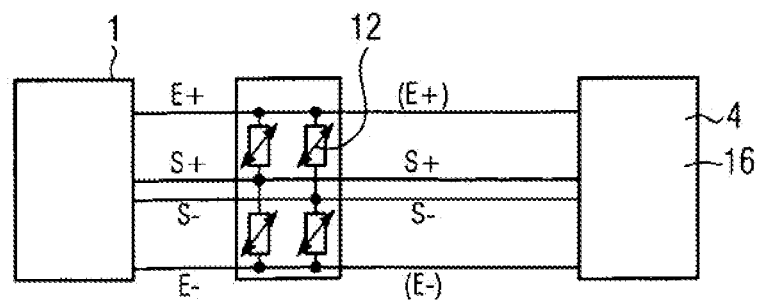
FIG. 4 shows schematically the electrical interconnections between the bedside monitor, the portable measurement device, and the disposable pressure transducer.

FIG. 4 schematically shows the electrical coupling of the pressure transducer 7 with both the bedside monitor 1 and the portable measurement device 4. To avoid the case that both the bedside monitor 1 and the portable measurement device 4 provides an excitation voltage for the pressure transducer 7 preferably at least the portable measurement device 4 can include a excitation sensing circuit 16 which detects via the excitation lines whether an excitation voltage is already supplied to the pressure transducer 7 and if an excitation voltage is already supplied to the pressure transducer 7 no excitation voltage is supplied by the portable measurement device 4. Otherwise the portable measurement device 4 supplies an excitation voltage to the pressure transducer 7 via excitation lines.

In general, each of the monitoring devices 1, 4 connected to the pressure transducer 7 may be configured to deliver an excitation voltage to the pressure transducer 7 if it is not present. In this configuration all monitoring devices to be coupled to the detector device could be built up equally and the monitoring device which provides the excitation to the detector device is defined on the fly.

As mentioned above, the pressure transducer 7 has to function with both configurations either connected to a bedside monitor 1 only or connected simultaneously to the bedside monitor 1 and the portable measuring device 4 in parallel.

The connection of the pressure transducer 7 to the bedside monitor 1 may be mandatory. Then, the pressure transducer 7 gets its excitation voltage from the bedside monitor 1. The portable measurement device 4 detects the excitation voltage and measures the sensor signal. However, the pressure reading on the bedside monitor 1 may under no circumstances be influenced by a parallel connection of the portable measurement device 4. As the portable measurement device 4 includes an input resistance the sensor signal is influenced by the input resistance of the sensing ports of the portable measurement device 4 if the portable measurement device 4 is connected to the cable connection. By providing the pressure transducer 7 with a Wheatstone bridge the sensitivity with regard to input resistances of portable measurement device 4 and/or the bedside monitor 1 are already substantially decreased. Furthermore, according to the present embodiment the connectors, i.e. the transducer plug A, the BSM plug C and the intermediate plug B of the portable measurement device 4 are provided with a structure which allows the bedside monitor 1 to detect the sensor signal from the pressure transducer 7 under the same conditions either with the portable measurement device 4 connected or not.

Figure 5:
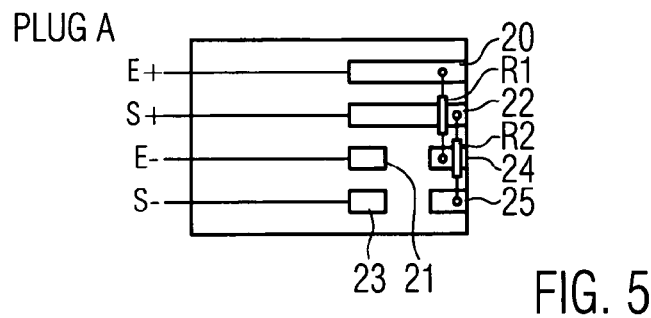
FIG. 5 schematically illustrates the terminals of the transducer plug A.

In FIG. 5 the terminals of the transducer plug A are schematically shown. The terminals for the provision of the excitation voltages to the pressure transducer 7 are referred to as first and second excitation terminals 20 and 21, respectively, the signal terminals for reading the sensor signals from the pressure transducer 7 are indicated as first and second signal terminals 22 and 23, respectively. The transducer plug A includes a first trimming resistance R1 and a second trimming resistance R2. The first trimming resistant is coupled between the first excitation terminal 20 and a third excitation voltage terminal 24. The second trimming resistance R2 is coupled between the first signal terminal 22 and a third signal terminal 25. The third excitation terminal 24 and the third signal terminal 25 are open that means they are not contacted in a non-contacting condition of the transducer plug A. Furthermore, the second excitation terminal 21 and the third excitation terminal 24 as well as the second signal terminal 23 and the third signal terminal 25 are fully isolated from each other.

The first and the second trimming resistances R1, R2 (impedances) have respective values that simulate the resistances (impedances) of the portable measurement device 4 if connected to the BSM plug A. Therefore, the value of the first trimming resistance R1 is selected to correspond to the internal resistance between the excitation terminal contacts of the portable measurement device 4. The value of the second trimming resistance R2 is selected to correspond to the internal input resistance of detection signal contacts of the portable measurement device 4 for receiving the sensor signal.

Figure 6:
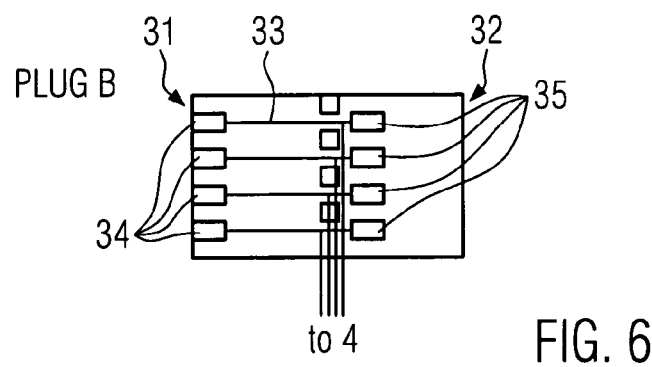
FIG. 6 schematically illustrates the terminals of the intermediate plug B.

In FIG. 6 the internal structure of the intermediate plug B is shown. The intermediate plug B provides interconnection wiring 33 for each of the excitation voltages E+, E− and each of the sensor signals S+, S− which are further branched to the portable measurement device 4 such that the portable measurement device 4 can provide an excitation voltage, receive an excitation voltage and may tap the sensor signal from the pressure transducer 7 via the transducer plug A. For coupling with the transducer plug A, the intermediate plug B has first contacts 34 of a first outlet 31. For coupling with the BSM plug C, the intermediate plug B has second contacts 35 of a second outlet 32. The first outlet 31 is structurally adapted to be only connectable to the transducer plug A wherein the second outlet 32 of the intermediate plug B is structurally adapted to be only connectable with the BSM plug C. Thereby, faulty interconnections between the devices can be avoided.

Figure 7:
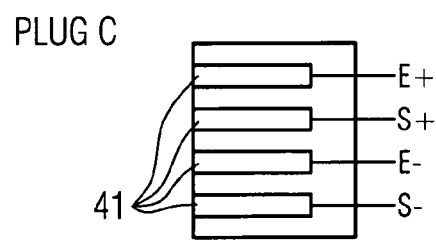
FIG. 7 schematically illustrates the terminals of the BSM plug C.

FIG. 7 illustrates the structure of the BSM plug C. The respective excitation lines E+, E− and sensor signal lines S+, S− connected with the bedside monitor 1 are coupled to respective contacts 41.

The BSM plug C can be connected with the second outlet 32 of the intermediate plug B such that the interconnection wiring 33 are in contact with the respective excitation lines E+, E− and the signal lines S+, S− of the BSM cable. The contacts 41 of the BSM plug C can be provided as long contact pads which are able to simultaneously contact, in a plugged condition with plug A, the second and third excitation terminal 21, 24 as well as the second and third signal terminals 23 and 25, respectively.

Figure 8:
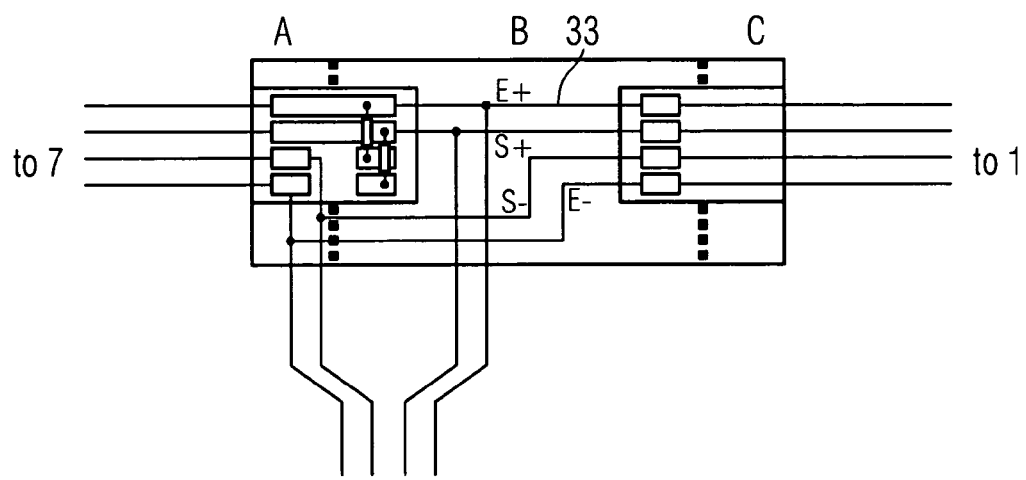
FIG. 8 shows the BSM plug C, the intermediate plug B and the transducer plug A in a connected condition.

As shown in FIG. 8, the BSM plug C, the intermediate plug B and the transducer plug A are connected with each other. An electrical interconnection of the excitation lines and signal lines between the transducer plug A and the BSM plug C is provided by the interconnection wiring 33 in the intermediate plug B. Furthermore the intermediate plug B provides the electrical connection of the interconnection wiring 33 with the portable measurement device 4 such that the portable measurement device 4 receives the excitation voltage as well as the sensor signals provided by the pressure transducer 7. When coupling the first outlet 31 of the intermediate plug B to the transducer plug A the first contacts 34 of the intermediate plug B do only connect the first and second excitation terminals 20, 21 and the first and second signal terminals 22, 23 of the transducer plug A, respectively. The third excitation terminal 24 and the third signal terminal 25 are not electrically contacted. One reason therefore is that between the first and second excitation terminals 20 and 21 of the transducer plug A a value of the first trimming resistance R1 is provided as the input resistance of the portable measurement device 4. Therefore the first trimming resistance R1 should not be electrically effective within the transducer plug A. The same is for the second trimming resistor R2 which also is electrically ineffective as the portable measurement device 4 is in electrical connection with the first and second signal terminals 22 and 23. To summarize, the trimming resistors (impedances) R1, R2 provided within the transducer plug A are made electrically ineffective as they are not necessary to simulate the internal resistances of the portable measurement device 4 as it is already connected.

Figure 9:
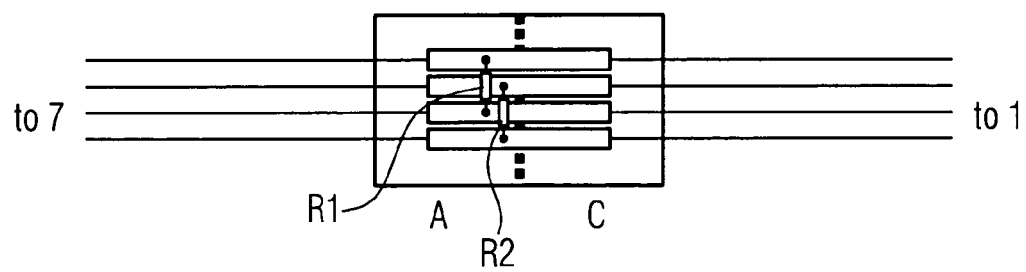
FIG. 9 shows the BSM plug C and the transducer plug A in a connected condition.

However, as shown in the configuration of FIG. 9 the BSM plug C is configured to be also connected with the transducer plug A. In such a configuration contacts of the BSM plug C contacts the second excitation voltage terminal 21 and the second signal terminal 23 in the manner described with regard to the connection with the intermediate plug B. However, the BSM plug C further provides an interconnection (shortcut) between the second excitation terminal 21 and the third excitation voltage terminal 24 as well as between the second signal terminal 23 and the third signal terminal 25. The shortcut make the first and second trimming resistors R1 and R2 electrically effective such that between the first and second excitation terminals 20, 21 as well as it been the first and second signal terminals 22 and 23 the trimming resistances (impedances) R1, R2 are applied which simulate the state of a connection of the portable measurement device 4 although it is not connected to the monitoring system in this configuration. As there is no portable measurement device 4 connected the trimming resistors R1, R2 are electrically effective.

The plugs A, B, C can be provided with terminals and contacts configured as simple contact pads, pins and the like which can be contacted with corresponding terminals and contacts which may be adapted like flexible contact beams, spring-like contacts and the like.

In general, features for connectors A, B, and C should fulfil following requirements:
- the transducer connector can be connected either with a first outlet of the intermediate connector B or with an monitoring device connector each for connecting the detector device with a respective monitoring device;
- a second outlet of the intermediate connector is only connectable with a monitoring device connector but not with the transducer connector;
- in case the transducer connector is directly connected with a monitoring device connector, trimming resistances are made electrically effective and coupled with at least one of excitation terminals and signal terminals of the transducer connector;
- in case the intermediate connector is connected with the transducer connector the trimming resistances R1, R2 are not made electrically effective.

The embodiments of the present invention provide at least one or more of the following advantages:
- an arterial blood pressure waveform can be measured by two or more monitoring devices in parallel using only one sensor known disadvantages of curve-damping by using two sensors which would result in a larger dead space within one pressure sensor are ruled out;

the pressure of exactly the same heart level can be recorded by two monitoring devices;

the pressure transducer can be trimmed to correct impedance conditions independently from whether it is connected to the bedside monitor alone or to both the bedside monitor and the portable measurement device in parallel;

the pressure transducer is only provided with one transducer plug which only has one outlet so safety requirements during defibrillation are fulfilled. In other words no open connection exists.

The principle of the present invention can be used for any passive analogue sensor like e.g. a thermostat for temperature measurement, a conductivity sensor or an electrical impedance sensor as long the additional measurement device has an adapted interface and its inner resistance (impedance) is known as constant.

Further to the embodiment of the monitoring system of FIGS. 1 and 3 the pressure transducer 7 can also be applied close to the catheter 9. Moreover, further connectors can be provided within the connection cables of all monitoring devices and the sensor device.

In the above-mentioned embodiment preferably both the bedside monitor 1 and the portable measurement device 4 are provided with a source for an excitation voltage. Both devices may be provided with excitation sensing circuits to decouple the excitation voltage if an excitation voltage is already present on the excitation lines in the cable connection between the respective measurement device and the pressure transducer 7. However, as portable measurement devices usually are battery powered it is preferred that the portable measurement device is the device which decouples the excitation voltage from the transducer in case the bedside monitor 1 may provide the excitation voltage. In other words, it can be provided that the provision of the excitation voltage by the bedside monitor 1 has priority to the provision of the excitation voltage by the portable measurement device 4.

Figure 10:
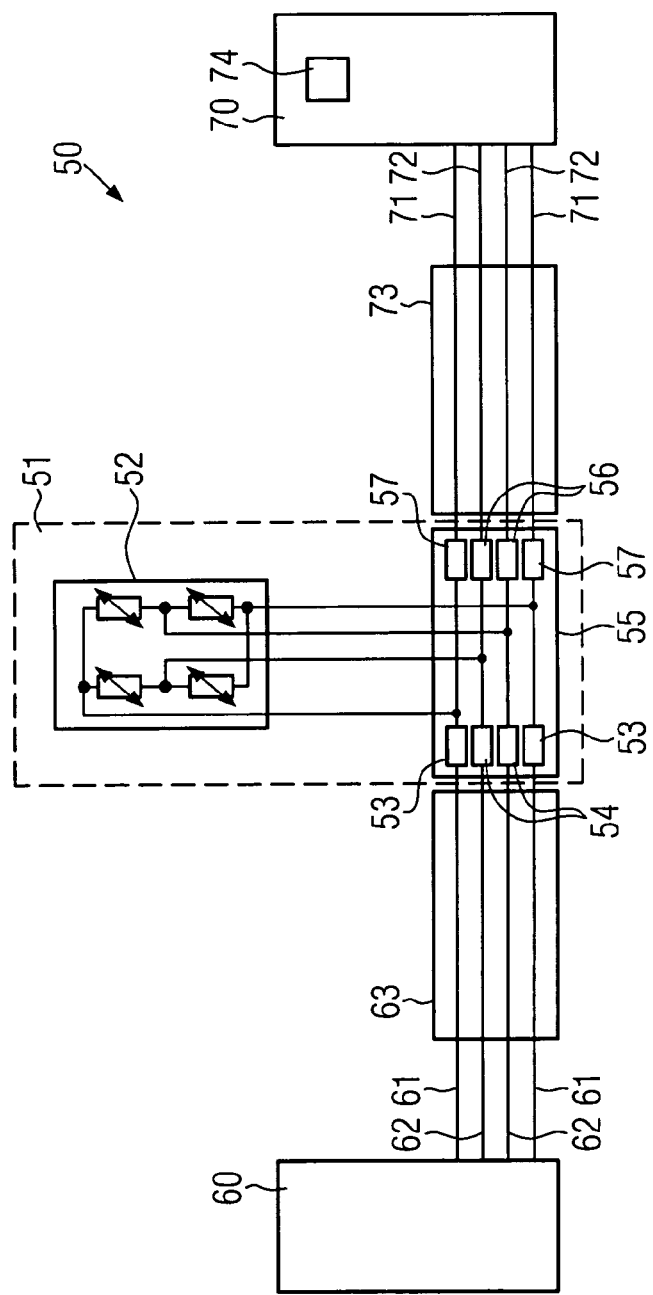
FIG. 10 shows a disposable sensor device and a monitoring system according to a further embodiment.

Another embodiment is shown in FIG. 10, wherein another structure of a disposable sensor device in a monitoring system is depicted. The monitoring system 50 of FIG. 10 includes a disposable sensor device 51 having a transducer 52 and a connector 55 having a first connector port to accommodate two first signal terminals 54 and two first supply terminals 53 as known from the embodiments described above. Preferably, the transducer 52 and the connector 55 may be integrally formed, however, they can also be connected together via a suitable cable. The circuitry of the transducer 52 (e.g. Wheatstone Bridge) may be similar or the same as of the above embodiments. Instead of a Wheatstone bridge a simple voltage divider comprising a series connection of two pressure sensors or of one pressure sensor and one or more resistors. A tap between the pressure sensors or between the pressure sensor and the resistors provides a single sensor signal based on the detected pressure.

The connector 55 is further provided with a second connector port accommodating second signal terminals 56 and, as an optional feature, second supply terminals 57, wherein each of the first supply terminals 53 is electrically interconnected with a respective second supply terminal 57 (if existing) and each of the first signal terminals 54 is electrically interconnected with a respective second signal terminal 56.

To the first connector port a first plug 63 may be connected to electrically connect a first monitoring device 60 to the disposable sensor device 51 via the first supply lines 61 and the first signal lines 62. Normally, the first monitoring device 60 provides an excitation voltage via the first supply lines to the disposable sensor device 51. The excitation voltage can be set as already explained with respect to the above embodiments.

The first monitoring device 60 receives a sensor signal via the first signal lines 62 from the disposable sensor device 51 to detect the quantity to be measured, such as the blood pressure of the patient, as already described above.

To the second connector port a second plug 73 may be connected to connect a second monitoring device 70 to the disposable sensor device 51 via the second supply lines 71 and the second signal lines 72. The second monitoring device 70 preferably merely receives a sensor signal via the second signal lines 62 from the disposable sensor device 51 to detect the quantity to be measured, but without supplying any supply to the disposable pressure device. In that case no supply lines need to be provided between the second plug 73 and the second monitoring device 70. Thereby, the second monitoring device 70 can be provided without a supply source for driving the sensor device 51 and the design effort for the second monitoring device 70 can be reduced.

According to another embodiment, the second monitoring device 70 may be provided with an excitation sensing circuit 74 which can be connected via second supply lines with the second supply terminals in the connector 55 of the disposable sensor device 51. The excitation sensing circuit 74 is adapted to detect whether or not an excitation is provided from the first monitoring device 60 via the first supply terminals 53 and supplies an excitation voltage by its own in case no excitation voltage can be detected via the second supply lines 71.

In case the transducer merely includes a voltage divider or another circuit instead of a Wheatstone bridge only one or more than two first and second signal lines 62, 72 as well as the respective connectors may be provided.

REFERENCE NUMERALS

1 Bedside monitor
2 arterial pressure module
3 Cable
4 portable measurement device
5 Tubing
6 pressure transducer cable
7 pressure transducer
8 organizer plate
9 catheter
11 reservoir
12 pressure detecting elements
16 Excitation sensing circuit
17 Stop cock
20 First excitation terminals
21 Second excitation terminals
22 First detection signal
23 Second detection signal
24 Third excitation terminals
25 Third detection signal
31 First outlet
32 Second outlet
33 Interconnection wiring
34 First contacts
35 Second contacts
41 Contacts
51 Disposable sensor device
52 Sensor
53 First supply terminal
54 First signal terminal 55 Connector
56 Second signal terminal
57 Second supply terminal
60 First monitoring device
61 First supply lines
62 First signal lines
63 First plug
70 Second monitoring device
71 First supply lines
72 First signal lines
73 Second plug
74 Excitation detection circuit

The invention claimed is:

1. A disposable sensor device for patient monitoring comprising:
   a sensor for providing an electric quantity based on a quantity to be detected;
   a first connector coupled to the sensor, the first connector comprising a first signal terminal, a second signal terminal and a third signal terminal, wherein the first signal terminal and the second signal terminal are adapted to provide the electrical quantity;
   a trimming element attached between the first signal terminal and the third signal terminal, wherein the trimming element is electrically isolated from the second signal terminal in a first configuration, and is electrically connected to the second signal terminal in a second configuration.

2. The disposable sensor device according to claim 1, wherein, in the first configuration, the first signal terminal and the second signal terminal are tapped for electrical connections and the third signal terminal remains untapped, and wherein, in the second configuration, the first signal terminal and the third signal terminal are tapped and a shortcut is established between the second signal terminal and the third signal terminal.

3. The disposable sensor device according to claim 2, wherein the electrical quantity is impedance and wherein the trimming element has a trimming impedance.

4. The disposable sensor device according to claim 1, wherein the sensor comprises a Wheatstone-Bridge circuit.

5. The disposable sensor device according to claim 1, wherein the sensor is a pressure sensor for measuring an arterial pressure of a patient.

6. The disposable sensor device according to claim 1, wherein a first excitation terminal is provided in the first connector to apply an excitation voltage to the sensor.

7. The disposable sensor device according to claim 6, wherein the first connector further comprises:
   a first excitation terminal, a second excitation terminal, and a third excitation terminal, wherein the first excitation terminal and the second excitation terminal are adapted to receive an excitation voltage; and
   a further trimming element attached between the first excitation terminal and the third excitation terminal, wherein, in the first configuration, the first excitation terminal and the second excitation terminal are connected to the excitation voltage and the third excitation terminal remains unconnected, and wherein in the second configuration, the first excitation terminal and the third excitation terminal are connected to the excitation voltage and a shortcut is established between the second excitation terminal and the third excitation terminal.

8. A monitoring system for patient monitoring comprising:
   a disposable sensor device comprising:
   a sensor for providing an electric quantity based on a quantity to be detected;
   a first connector coupled to the sensor, the first connector comprising a first signal terminal, a second signal terminal and a third signal terminal, wherein the first signal terminal and the second signal terminal are adapted to provide the electrical quantity;
   a trimming element attached between the first signal terminal and the third signal terminal, wherein the trimming element is electrically isolated from the second signal terminal in a first configuration, and is electrically connected to the second signal terminal in a second configuration; and
   a first monitoring device for tapping the electric quantity, the first monitoring device comprising a second connector to match with the first connector.

9. The monitoring system according to claim 8, wherein the second connector has a terminal contact to shortcut the second signal terminal and the third signal terminal of the first connector when the second connector is connected with the first connector such that the trimming element is electrically connected to the second signal terminal.

10. The monitoring system according to claim 8, wherein the first connector further comprises:
    a first excitation terminal, a second excitation terminal, and a third excitation terminal, wherein the first excitation terminal and the second excitation terminal are adapted to receive an excitation voltage; and
    a further trimming element attached between the first excitation terminal and the third excitation terminal,
    wherein the second connector has an excitation terminal contact which is adapted to provide the excitation voltage from the first monitoring device and to shortcut the second excitation terminal and the third excitation terminal of the first connector when the second connector is connected with the first connector such that the further trimming element is electrically connected to the second excitation terminal.

11. A monitoring system for patient monitoring comprising:
    a disposable sensor device comprising:
      a sensor for providing an electric quantity based on a quantity to be detected;
      a first connector coupled to the sensor, the first connector comprising a first signal terminal, a second signal terminal, and a third signal terminal, wherein the first signal terminal and the second signal terminal are adapted to provide the electrical quantity;
      a trimming element attached between the first signal terminal and the third signal terminal, wherein the trimming element is electrically isolated from the second signal terminal in a first configuration, and is electrically connected to the second signal terminal in a second configuration;
    a second monitoring device for tapping the electric quantity, the second monitoring device comprising a third connector to match with the first connector, wherein the third connector has a connector structure such that, when the first connector and the third connector are connected, the trimming element of the first connector is electrically isolated from the second signal terminal.

12. The monitoring system according to claim 11,
    wherein the third connector has a terminal contact to only contact the second signal terminal but not the third signal terminal of the first connector when the first connector and the third connector are connected such that the trimming element is electrically isolated from the second signal terminal.

13. The monitoring system according to claim 11, wherein the first connector further comprises:

a first excitation terminal, a second excitation terminal, and a third excitation terminal, wherein the first excitation terminal and the second excitation terminal are adapted to receive an excitation voltage; and a further trimming element attached between the first excitation terminal and the third excitation terminal of the first connector, and wherein the third connector has an excitation terminal contact which is adapted to provide the excitation voltage from the second monitoring device and to only contact the second excitation terminal but not the third excitation terminal of the first connector when the first connector and the third connector are connected such that the further trimming element is electrically isolated from the second excitation terminal.

14. A monitoring system for patient monitoring comprising:

a disposable sensor device comprising:

a sensor for providing an electric quantity based on a quantity to be detected;

a first connector coupled to the sensor, the first connector comprising a first signal terminal, a second signal terminal, and a third signal terminal, wherein the first signal terminal and the second signal terminal are adapted to provide the electrical quantity;

a trimming element attached between the first signal terminal and the third signal terminal, wherein the trimming element is electrically isolated from the second signal terminal in a first configuration, and is electrically connected to the second signal terminal in a second configuration;

a first monitoring device for tapping the electric quantity, the first monitoring device comprising a second connector to match with the first connector;

a second monitoring device for tapping the electric quantity, the second monitoring device comprising a third connector having two outlets to respectively match with the first connector and the second connector, wherein the third connector has a connector structure such that, when the first connector and the third connector are connected the trimming element of the first connector is electrically isolated from the second signal terminal and the second monitoring device receives the electrical quantity passed through the third connector.

15. The monitoring system according to claim 14, wherein the second connector has a terminal contact which is adapted to shortcut the second signal terminal and the third signal terminal of the first connector when the first connector and the second connector are connected such that the trimming element is electrically connected to the second signal terminal, wherein the third connector has a terminal contact which is adapted to only contact the second signal terminal but not the third signal terminal of the first connector such that the trimming element is electrically isolated from the second signal terminal.

16. The monitoring system according to claim 14, wherein the first connector further comprises:

a first excitation terminal, a second excitation terminal, and a third excitation terminal, wherein the first excitation terminal and the second excitation terminal are adapted to receive an excitation voltage; and a further trimming element attached between the first excitation terminal and the third excitation terminal of the first connector, wherein the second connector has an excitation terminal contact which is adapted to shortcut the second excitation terminal and the third excitation terminal to both connect them with the excitation voltage when the first connector and the second connector are connected, wherein the third connector has an excitation terminal contact which is adapted to only contact the second excitation terminal but not the third excitation terminal of the first connector when the first connector and the third connector are connected such that the further trimming element is electrically isolated from the second excitation terminal, wherein the third connector further has a connector structure such that when the first connector, the second connector, and the third connector are connected, the first monitoring device is adapted to supply the excitation voltage to the sensor via the third connector.

17. The monitoring system according to claim 14, wherein the second monitoring unit further comprises an excitation sensing circuit, which is adapted to detect, whether an excitation voltage is applied on the first excitation terminal and the second excitation terminal of the first connector when the first connector and the third connector are connected, and wherein the excitation sensing circuit is further adapted to supply the excitation voltage via the third connector to the first connector when no excitation voltage is detected, and to supply no excitation voltage when the excitation voltage is detected.

18. The monitoring system according to claim 14, wherein the second monitoring device is adapted to monitor the quantity to be detected when the trimming element and the further trimming element are electrically connected to the second signal terminal and the second excitation terminal, respectively.

* * * * *